United States Patent
Imran

[11] Patent Number: 5,976,169
[45] Date of Patent: Nov. 2, 1999

[54] STENT WITH SILVER COATING AND METHOD

[75] Inventor: Mir A. Imran, Los Altos Hills, Calif.

[73] Assignee: CardioVasc, Inc., Menlo Park, Calif.

[21] Appl. No.: 09/201,074

[22] Filed: Nov. 30, 1998

Related U.S. Application Data

[63] Continuation-in-part of application No. 08/991,383, Dec. 16, 1997, abandoned.

[51] Int. Cl.$^6$ .................................................. A61M 29/02
[52] U.S. Cl. .......................... 606/194; 427/2.24; 427/2.3; 604/265; 606/191; 606/195; 606/198; 607/116; 607/75; 623/1; 623/11
[58] Field of Search ........................... 427/2.1, 2.3, 2.28, 427/2.25; 607/116, 75; 604/265; 606/191, 194, 195, 198; 424/423; 623/1, 11

[56] References Cited

U.S. PATENT DOCUMENTS

| | | | |
|---|---|---|---|
| 3,932,627 | 1/1976 | Margraf | 424/183 |
| 5,295,979 | 3/1994 | DeLaurentis et al. | 604/265 |
| 5,360,440 | 11/1994 | Andersen | 607/116 |
| 5,419,760 | 5/1995 | Narisco, Jr. | 604/8 |
| 5,449,382 | 9/1995 | Dayton | 623/1 |
| 5,464,650 | 11/1995 | Berg et al. | 427/2.3 |
| 5,498,248 | 3/1996 | Midler | 604/265 |
| 5,534,287 | 7/1996 | Lukic | 427/2.25 |
| 5,567,495 | 10/1996 | Modak et al. | 428/36.9 |
| 5,609,629 | 3/1997 | Fearnot et al. | 623/1 |
| 5,665,103 | 9/1997 | Lafontaine et al. | 606/192 |
| 5,741,327 | 4/1998 | Frantzen | 623/1 |
| 5,770,255 | 6/1998 | Burrell et al. | 427/2.1 |
| 5,824,045 | 10/1998 | Alt | 623/1 |
| 5,824,049 | 10/1998 | Ragheb et al. | 623/1 |
| 5,824,077 | 10/1998 | Mayer | 623/11 |
| 5,873,904 | 2/1999 | Ragheb et al. | 623/1 |
| 5,888,577 | 3/1999 | Griffin, III et al. | 427/2.3 |
| 5,897,911 | 4/1999 | Loeffler | 427/2.3 |

*Primary Examiner*—Diana Dudash
*Attorney, Agent, or Firm*—Flehr Hohbach Test Albritton & Herbert

[57] ABSTRACT

A stent comprising a cylindrical member formed of metal and having a wall defining a bore extending therethrough along a longitudinal axis and having an inner surface and an outer surface. The wall has a pattern formed therein with openings extending therethrough into the bore. A coating containing silver is adherent to the outer surface of said wall for treatment of undesired conditions in the vessel.

5 Claims, 1 Drawing Sheet

STENT WITH SILVER COATING AND METHOD

This application is a continuation-in-part of application Ser. No. 08/991,383 filed on Dec. 16, 1997, now abandoned.

This invention relates to a stent with a silver coating and method.

Stents have heretofore been utilized to maintain openings through stenoses in vessels in the human body and in particular in the vessels of the heart. It has now been become relatively widely known that restenosis occurs inside stents. Also it has been known that during the placement of a stent in a vessel there is damage to the wall of the vessel which encourages smooth muscle cell proliferation that may encourage the occurrence of restenosis within the stent itself. There is therefore a need for a new and improved stent which overcomes such difficulties.

In general, it is an object of the present invention to provide a stent which is provided with a silver coating for treatment of a stenosis in a vessel.

Another object of the invention is to provide a stent of the above character which inhibits smooth muscle cell proliferation.

Another object of the invention is to provide a standard method of the above character for reducing the possibility of restenosis within the stent.

Another object of the invention is to provide a stent of the above character which is coated with silver to utilize the capability of silver for the treatment of diseases of the vessel.

Another object of the invention is to provide a stent of the above character which is utilized for treatment of bacteria in the vessel.

Additional objects and features of the invention will appear from the following description in connection with the accompanying drawings.

Figure 2:
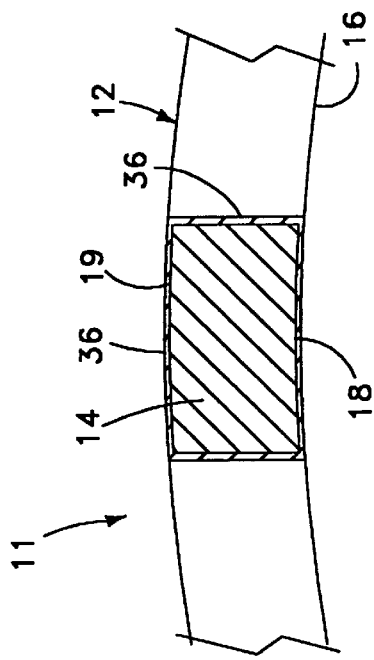
FIG. 2 is a cross sectional view taken along the line 2—2 of FIG. 1.

In general, the stent of the present invention is comprised of a cylindrical member formed of metal and having a wall defining a bore extending therethrough along a longitudinal axis and having an inner surface and an outer surface. The wall has a pattern formed therein with openings therein extending into the bore. A coating of silver is adherent to the outer surface of the wall of the cylindrical member.

In the method for treating vessels having a stent therein formed of metal having a wall defining a bore extending therethrough along a longitudinal axis and having an inner surface and an outer surface, the wall having a pattern formed therein having openings extending therethrough into the bore. The method comprises the step of coating the inner and outer surfaces of the member with silver to thereby utilize silver for its beneficial effects for the prevention of smooth muscle cell growth and for inhibiting restenosis within the stent and for the treatment of diseases in the vessel.

More in particular, the stent 11 of the present invention is comprised of a cylindrical member 12 which is comprised of at least one and preferably a plurality of segments 13. Each of the segments 13 has a wall 14 defining a bore 16 extending therethrough along a longitudinal axis 17. The wall is provided with inner and outer surfaces 18 and 19. The metal preferably used for the wall 14 is stainless steel. However, other metals such as nickel-titanium alloys can be used if desired.

Figure 1:
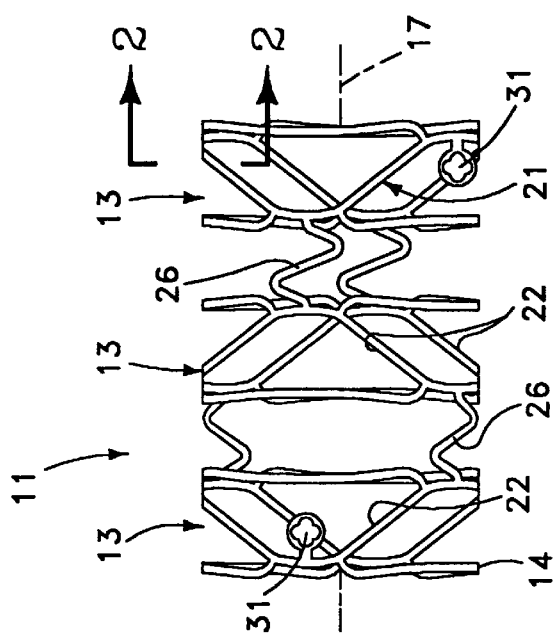
FIG. 1 is a side elevational view of a stent incorporating the present invention.

A pattern 21 is formed in the wall 14 and is of a type described in co-pending application Ser. No. 08/991,384, filed Dec. 16, 1997, which has openings 22 extending therethrough from the outer surface into the bore 16. As shown in FIG. 1, a plurality of segments 13 are provided. Means is provided for interconnecting the segments and consists of interconnecting links 26 which can be substantially S-shaped as described in co-pending application Ser. No. 08/991,384, filed Dec. 16, 1997. As explained in the co-pending application, the links serves to accommodate shrinkage of the segments 13 as the stent 11 is expanded and serves to maintain the length of the stent during such expansion.

Radiopaque markers 31 of the type described in co-pending application Ser. No. 08/991,378, filed Dec. 16, 1997, are provided within openings 22 of the pattern 21.

In accordance with the present invention and as shown in FIGS. 1 and 2, the cylindrical member 12 is coated with a layer 36 containing silver or alloys thereof which covers the inner and outer surfaces 18 and 19 of the wall 14 of each of the segments as well as the interconnecting links 26 and the radiopaque markers 31. This coating of silver can be accomplished in any suitable manner such as by electroplating, sputtering or by dipping in a silver loaded polymer to achieve the proper thickness for the silver coating. Typically a thickness ranging from 0.0002" 0.001" can be provided and preferably a thickness of 0.0005" is provided.

Figure 3:
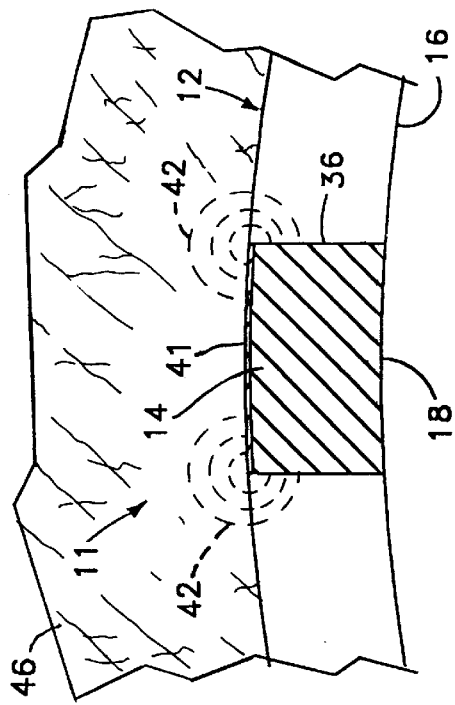
FIG. 3 is an alternative cross sectional view taken along the line 2—2 of FIG. 1.

As shown in the alternative embodiment in FIG. 3, it has been found that improved results can be obtained by placing the silver coating of the type hereinbefore described as a layer of silver 41 on only the outer surface 19 of the wall 14 which as hereinbefore described is formed of stainless steel. It has been found that the silver in conjunction with the stainless steel forms a bimetallic coupling which creates electromotive forces represented by the lines 42 as shown in FIG. 3 which extend from the outside of the silver layer 41 to the side walls of the wall 14. Thus a bimetallic action is created between the layer 41 and the exposed sides of the wall 14 forming a part of a segment 13. This creation of these electromotive force lines serves to drive the silver ions into the adjacent tissue 46 with greater efficacy to enhance the effects hereinbefore described. Thus it can be seen that providing the silver only on one side and thereby creating a bimetallic coupling, electromotive forces are created which drive the silver ions deep into the surrounding tissue.

In conjunction with the foregoing it should be appreciated when the layer of silver is referred to that this can include any coating which includes silver as for example a silver ion containing coating, a silver alloy or a silver bearing compound.

Since mechanical devices such as stents are already utilized for keeping atherosclerotic diseased arteries patent or open, these stents can also be utilized for an additional purpose for the treatment of conditions occurring in the vessel and in which they are disposed and also for the treatment of diseases in the vessel in which they are disposed. This is advantageous because the silver carried by the stent produces silver ions within the vessel which migrate into adjacent tissue and thus would interact with smooth muscle cells that are in close proximity to the stent. These smooth muscle cells are present in inner and outer surfaces and in the medial layer of the arterial wall.

Typically after stent deployment in a vessel injury occurs in the vessel which causes the vessel to attempt to repair the injury. Often the body's response to such injury overshoots and causes smooth muscle cells to proliferate at a rapid rate due to the openings in the pattern of the stent and thereby cause restenosis within the stent. The generation of silver ions inhibits smooth muscle cell proliferation within the stent. In addition, the generation of silver ions by the stent is also directly effective against diseases in the vessel such as any bacterial or viral infection occurring in atherosclerotic plaque.

In other words the silver ions act as a broad spectrum antibiotic and are beneficial to patients to treat undesired conditions in a vessel and particularly infections in the arterial walls of a vessel by killing such bacteria. Such silver ions since they are highly reactive are also capable of stopping smooth muscle cell proliferation by extensively reacting with growth factors that signal the cells to divide and then are released by the cells. Thus it can be seen that by providing a stent with a silver based coating thereon a number of efficacious effects are achieved.

What is claimed:

1. A stent for use in a vessel formed of tissue comprising a cylindrical member formed of metal and having a wall defining a bore extending therethrough along a longitudinal axis, the wall having an inner surface and an outer surface, said wall having a pattern formed therein with openings extending therethrough into the bore and a coating containing silver adherent solely to the outer surface of said wall for forming a bimetallic coupling between the coating and the metal to create electromotive forces which drive silver ions into the surrounding tissue.

2. A stent as in claim 1 wherein said metal is stainless steel.

3. A stent as in claim 1 wherein said coating is a silver compound.

4. A stent as in claim 1 wherein said coating is pure silver.

5. A method for treating vessels formed of tissue and having a stent therein formed of metal and having a wall defining a bore extending therethrough and having an inner surface and an outer surface, said wall having a pattern formed therein with openings therein extending into the bore, comprising the step of coating solely the outer surface of the cylindrical member with a coating containing silver for producing silver ions for the treatment of undesired conditions within the vessel and for creating a bimetallic coupling between the silver and the metal to thereby create electromotive forces for driving silver ions into the surrounding tissue.

\* \* \* \* \*